United States Patent
Kohashi

(10) Patent No.: US 7,985,952 B2
(45) Date of Patent: Jul. 26, 2011

(54) CHARGED PARTICLE SPIN POLARIMETER, MICROSCOPE, AND PHOTOELECTRON SPECTROSCOPE

(75) Inventor: Teruo Kohashi, Hachioji (JP)

(73) Assignee: Hitachi, Ltd., Tokyo (JP)

( * ) Notice: Subject to any disclaimer, the term of this patent is extended or adjusted under 35 U.S.C. 154(b) by 551 days.

(21) Appl. No.: 12/028,996

(22) Filed: Feb. 11, 2008

(65) Prior Publication Data
US 2008/0217533 A1    Sep. 11, 2008

(30) Foreign Application Priority Data

Mar. 5, 2007   (JP) ................................. 2007-053614
Jan. 9, 2008   (JP) ................................. 2008-002093

(51) Int. Cl.
*G01N 23/00*   (2006.01)
(52) U.S. Cl. ...... 250/310; 250/306; 250/307; 250/492.1
(58) Field of Classification Search .................. None
See application file for complete search history.

(56) References Cited

U.S. PATENT DOCUMENTS

| | | | | |
|---|---|---|---|---|
| 4,658,138 A * | 4/1987 | Koike et al. | ..................... | 250/310 |
| 5,444,243 A * | 8/1995 | Kohhashi et al. | ............. | 250/305 |
| 5,612,535 A * | 3/1997 | Wang | ............................. | 250/310 |
| 5,838,020 A * | 11/1998 | Hurt | ................................. | 257/10 |
| 5,936,244 A * | 8/1999 | Yajima et al. | .................. | 250/310 |
| 6,147,894 A * | 11/2000 | Hurt | ................................. | 365/118 |
| 6,337,540 B1 * | 1/2002 | Corbin et al. | ............. | 315/111.21 |
| 6,455,848 B1 * | 9/2002 | Krijn et al. | ..................... | 250/310 |
| 6,583,410 B1 * | 6/2003 | Seddon | ......................... | 250/305 |
| 6,639,218 B2 * | 10/2003 | Mukasa et al. | ..................... | 850/9 |
| 7,164,139 B1 * | 1/2007 | Toth et al. | ............... | 250/396 ML |
| 2004/0247796 A1 * | 12/2004 | Hanley et al. | .................. | 427/525 |
| 2008/0196619 A1 * | 8/2008 | Morency et al. | ........... | 106/14.05 |
| 2009/0095923 A1 * | 4/2009 | Gierak | ..................... | 250/492.21 |

FOREIGN PATENT DOCUMENTS

| | | | |
|---|---|---|---|
| JP | 60-177539 | | 9/1985 |
| JP | 7-174831 | | 7/1995 |
| JP | 07282767 A | * | 10/1995 |
| JP | 08241690 A | * | 9/1996 |
| JP | 2001-099815 | | 4/2001 |

OTHER PUBLICATIONS

New Physics Series 27 "Spin and Polarization" published by Baifukan in Oct. 1994, pp. 62-65.
New Physics Series 27 "Spin and Polarization" published by Baifukan in Oct. 1994, pp. 57-60.
"Systematic Experiment of Mott Scattering" by Teruo Kohashi, et al., Japanese Journal of Applied Physics, vol. 45, No. 8A, 2006, pp. 6468-6474.

(Continued)

*Primary Examiner* — Bernard E Souw
*Assistant Examiner* — Andrew Smyth
(74) *Attorney, Agent, or Firm* — Mattingly & Malur, PC

(57) ABSTRACT

A charged particle spin polarimeter that is capable of resolving with high efficiency the magnetic moment of a charged particle. The charged particle spin polarimeter has a pair of convex and concave magnetic poles to apply a magnetic field with gradient to an incident charged particle and a pair of plain plate electrodes to apply, to a charged particle, an electric field for canceling a Lorentz force that the charged particle receives from the magnetic field. The magnetic moment in the magnetic field direction of a charged particle is resolved by the interaction between the gradient of the magnetic field and the magnetic moment of the charged particle.

15 Claims, 9 Drawing Sheets

OTHER PUBLICATIONS

"Construction of a Compact Spin-and Angle-Resolved Photoelectron Spectrometer" by N. Takahashi, et al., JPN. J. Appl. Phys. vol. 35, (1996) pp. 6314-6319, Part 1, No. 12A, Dec. 1996.

"A Spin Rotator for Detecting All Three Magnetization Vector Components by Spin-Polarized Scanning Electron Microscopy" by T. Kohashi, et al.

* cited by examiner

CHARGED PARTICLE SPIN POLARIMETER, MICROSCOPE, AND PHOTOELECTRON SPECTROSCOPE

CLAIM OF PRIORITY

The present application claims priority from Japanese applications JP2007-053614 filed on Mar. 5, 2007 and JP2008-2093 filed on Jan. 9, 2008, the contents of which are hereby incorporated by reference into this application.

BACKGROUND OF THE INVENTION

The present invention relates to an analyzer that operates within a vacuum chamber and detects the magnetic moment of individual charged particles.

The Stern Gerlach method is known as a technique to resolve the spin of a neutron (New Physics Series "Spin and Polarization" p 57 published by Baifukan in October 1994). FIGS. 1A and 1B show the principle of the technique. First, as in FIG. 1A, a space is assumed where a magnetic field with large vertical component is applied to the orbit of a neutron 104 and the magnetic strength of the field has a gradient in the vertical direction. The magnetic field is applied by a pair of magnetic poles disposed perpendicular to the traveling direction of the neutron 104. One of the magnetic poles has a concave surface with respect to the orbit of the neutron, and the other magnetic pole has a convex surface against the convex plane. The magnetic field with gradient described above is formed when a magnetic field generated from the convex magnetic pole reaches the concave surface. Here, density of the magnetic field lines is higher at the upper region as seen from the charged particle orbit. When neutrons each having opposite-directed magnetic moment, namely parallel or unparallel to the direction of the magnetic gradient are radiated as shown in FIG. 1B, each neutron receives upward or downward force and thereby the orbit changes to allows the magnetic moments to be resolved. Even if the force from magnetic gradient is very small, since no other forces act on the neutrons resolution of the magnetic moment due to orbit change is enabled. Furthermore, if magnetic moment of the neutron has a horizontal component, that component precesses around the magnetic field direction as an axis of rotation and therefore is not kept constant and also will not receive the force caused by magnetic gradient. Several patents on the detection of magnetic moment using this method have been disclosed (for example, JP-A 2001-099815 and JP-A 1995-174831).

Since the separation of neutron orbits due to the effect described above is very small, actually a method of using the difference in convergence action due to the direction of magnetic moment is developed by means of the Rabi method in which the these two methods are combined (New Physics Series 27 "Spin and polarization" p 62 published by Baifukan in October 1994).

BRIEF SUMMARY OF THE INVENTION

However, the Stern Gerlach method cannot be applied to charged particles such as electrons and ions. This is because, when a charged particle passes through a magnetic field, the charged particle receives a Lorenz force that overwhelmingly larger than the force which magnetic moment receives from the magnetic field gradient, even if it is a minor energy of several eVs, and consequently it becomes impossible to resolve the difference in orbit due to the force exercised by the magnetic field gradient to magnetic moment. For example, in FIGS. 1A and 1B, assuming that the neutrons are charged particles, the charged particles receive vertical forces due to the interaction between their magnetic moments and magnetic field gradients, but the charged particles receive substantially larger horizontal Lorenz forces. In addition, since those Lorenz forces differ with the positions of the charged particles due to presence of the magnetic field gradients, the orbits of the charged particles disperse. As a result, it becomes impossible to resolve the magnetic moment according to the orbit. Therefore, techniques such as the Mott scattering (Jpn. J. Appl. Phys. 45, 6468, (2006) whose efficiency is more than three orders of magnitude lower than that of a common electron polarimeter is mainly used as the method of detecting, for example, the magnetic moment of an electron.

An object of the present invention is to provide a charged particle spin polarimeter capable of resolving with high-efficiency the magnetic moment of a charged particle, and various applied devices using it.

In order to achieve the above object, the present invention includes a pair of magnetic poles to apply a magnetic field having a gradient to an incident charged particle; and an electrode to apply an electric field to cancel a Lorenz force that is received by the charged particle from the magnetic field, and constitutes the charged particle spin polarimeter that resolves the magnetic moment in the magnetic field direction of the charged particle by means of the interaction between the magnetic field and the magnetic moment of a charged particle, and applied devices using it.

In the present invention, shape of the magnetic poles and electrodes is very important, and it is easy to form a magnetic field gradient on the orbit of a charged particle by using different types of magnetic poles, such as convex and concave types for N-side and S-side respectively. Furthermore, such an electrode as one that cancels the Lorenz force which a charged particle receives on its orbit is preferable, rather than one which generates a uniform electric field. For example, two plane electrodes are disposed at an inclined angle and not in parallel to each other. Also, the pair of electrodes is composed of hyperbolic or approximately hyperbolic square columns.

According to the present invention, it is possible to provide a dramatically efficient charged particle spin polarimeter capable of resolving the magnetic moment of each charged particle.

BRIEF DESCRIPTION THE DRAWINGS

DETAILED DESCRIPTION OF THE INVENTION

The present invention provides a polarimeter that resolves with high efficiency the magnetic moment of a charged particle. Before describing various embodiments of the present invention, the basic configuration of the polarimeter is described with reference to FIGS. 2A, 2B, and 3.

Figure 1A:
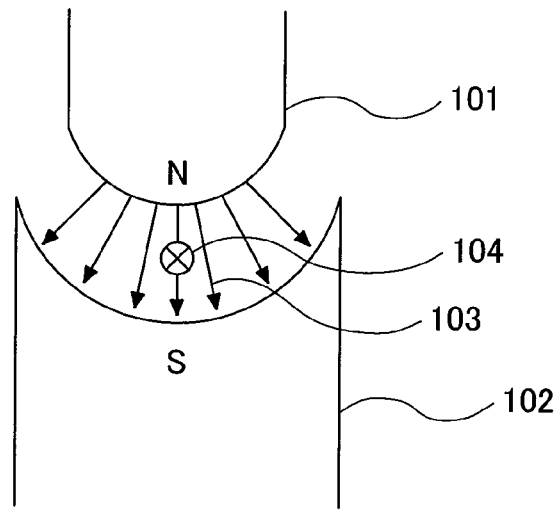
FIG. 1A shows the positional relation between magnetic poles and a magnetic field and neutrons generated thereby, in order to explain the principle of the Stern Gerlach method whereby the magnetic moment is resolved.
Figure 1B:
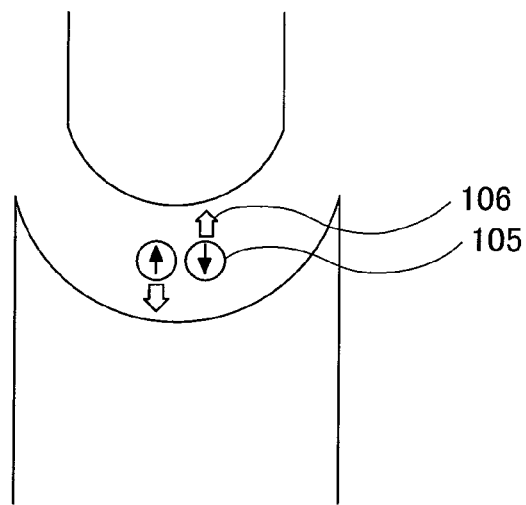
FIG. 1B shows the force that the magnetic moments of neutrons receives from magnetic field gradient, in order to explain the principle of the Stern Gerlach method whereby the magnetic moment is resolved.
Figure 2A:
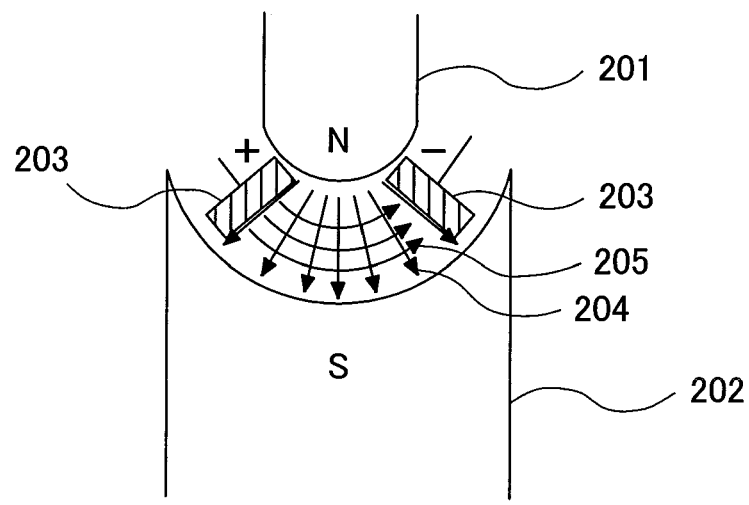
FIG. 2A shows the relation between the electrodes of a charged particle spin polarimeter of the present invention and the magnetic field and electric field generated thereby.
Figure 2B:
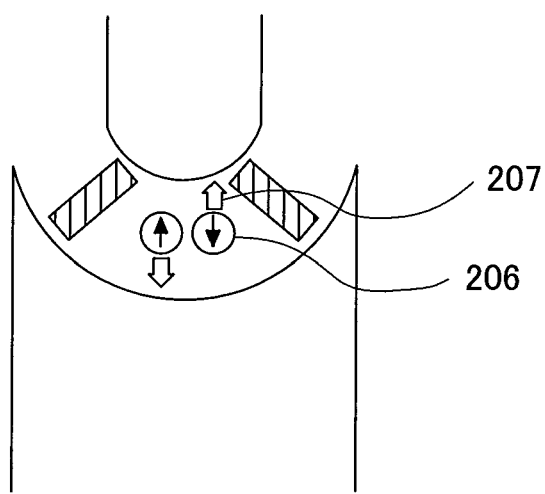
FIG. 2B shows the magnetic moments of charged particles and the force received thereby from magnetic gradient in a charged particle spin polarimeter of the present invention.

FIGS. 2A and 2B shows the basic configuration of the charged particle spin polarimeter of the present invention. As shown in FIG. 2A, like in the Stern Gerlach method, the N magnetic pole 201 and the S magnetic pole 202 are different in shape, and in the configuration shown in FIG. 2A the S magnetic pole has a concave surface and the N magnetic pole has a convex surface against the orbit of an incident charged particle. Although the two electrodes 203 are of the same plain, plate, a curved electric field is formed by tilting the electrodes relative to the longitudinal central axis of the N magnetic pole. The magnetic field line 204 and the electric flux line 205 generated in this state differ in direction and/or density with location. In this state, the charged particle 206 is radiated in the direction perpendicular to the drawing. The charged particle receives a Lorenz force from the magnetic field line, but receives an electrostatic force from the electric flux line 205 so as to cancel the Lorenz force. That is, it is necessary to generate such magnetic field line 204 and electric flux line 205. In that case, since the force the charged particle 206 receives is only the force 207 received from magnetic field gradient and that force is different in direction with the magnetic moment 206 of the charged particle, it is possible to resolve the magnetic moment of the charged particle as the difference in orbit.

Figure 3:
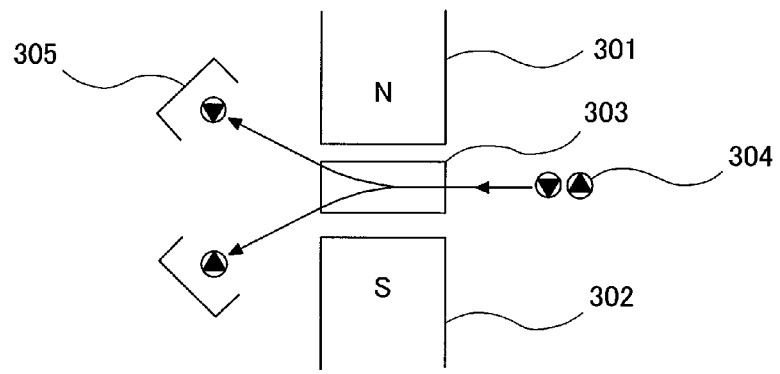
FIG. 3 shows how the orbit of a charged particle is resolved in a charged particle spin polarimeter of the present invention.

FIG. 3 shows the cross section of the charged particle spin polarimeter shown in FIGS. 2A and 2B, taken along the vertical direction of the drawing of FIG. 2B. In this figure, the charged particle 304 is radiated from the right side toward the magnetic poles 301 and 302 and the electrode 303, and receives there a force corresponding to the magnetic moment from magnetic field gradient and thereby the orbit changes while the charged particle passes through the magnetic poles 301 and 302 and the electrode 303. The charged particles whose orbits have been separated from each other are caught respectively by a charged particle polarimeter 305 to allow their magnetic moments to be resolved.

The efficiency of a conventional Mott polarimeter is about $1 \times 10^{-4}$ and improvement of the efficiency is a big challenge. With the spin polarimeter of the present invention, there is a possibility of increasing the efficiency to 1 theoretically if separation of the orbits from magnetic field gradient can be substantially large. That is, it is possible to achieve the efficiency 4 orders of magnitude higher than that of the conventional Mott polarimeter.

For the deflection due to a force electron spin receives from the magnetic field gradient, the deflection an electron accelerated by 10V receives while traveling one meter through 1 T/m magnetic field gradient is 1.4 um. This deflection is proportional to the $2^{nd}$ power of the traveling distance of the electron.

Also, using magnetic poles having different-shaped N-side and S-side as described above allows easy generation of magnetic field gradient on the orbit of a charged particle. Furthermore, since the electrode will not generate a uniform electric field but generate an electric field that cancels the Lorenz force a charged particle receives on its orbit, it is conceivable for example to dispose two plane plate electrodes inclined rather than in parallel. Also, it is possible to use a hyperbolic or approximately hyperbolic square column for the electrode. By making the surface profile (at least the side facing the orbit of a charged particle beam) hyperbolic or square, equi-electric potential plane or equi-magnetic potential plane becomes hyperbolic and thereby excellent convergence can be achieved.

Embodiment 1

Embodiment 1 is described below with reference to FIG. 4.

Figure 4:
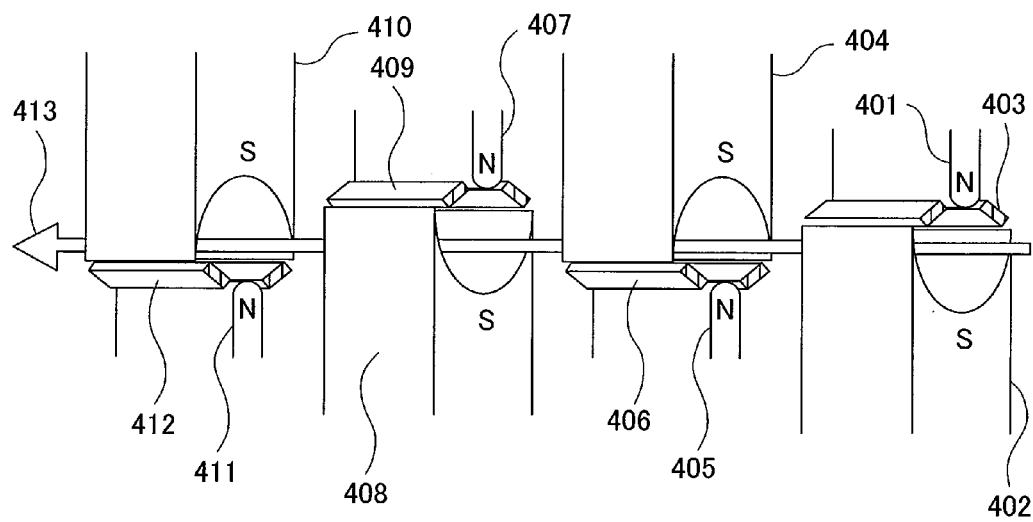
FIG. 4 shows the configuration of a charged particle spin polarimeter according to Embodiment 1.

FIG. 4 shows Embodiment 1 based on the basic configuration described in FIGS. 2A, 2B, and 3. Plural combinations of the magnetic poles and electrodes are arranged in the orbit of a charged particle. If a force the magnetic moment of a charged particle receives from the magnetic field gradient of a pair of magnetic pole and electrode is insufficient, a sufficient orbital change can be achieved by arranging plural such pairs and integrating the force received from the magnetic field gradient.

In this embodiment, a charged particle is first radiated to the magnetic poles 401 and 402 and the electrode 403. Here, as in the basic configuration, the Lorenz force and the electrostatic force are canceled. Then, the charged particle is radiated to the magnetic poles 404 and 405 and the electrode 406. Here, since the magnetic poles 401 and 402 and the magnetic poles 404 and 405 are designed to generate opposite magnetic fields to each other and also to be opposite in shape, the density distribution of magnetic field lines also become opposite. This results in the magnetic field gradients being the same. Therefore, the forces the magnetic moment of the charged particle receives from the magnetic field gradient generated by the magnetic poles 401 and 402 and the magnetic poles 404 and 405 have the same direction. However, since the direction of the magnetic fields generated by the respective magnetic poles are different, the Lorenz forces become opposite to each other and can be canceled. That is, even if the Lorenz forces cannot be canceled completely by the electrostatic forces, it is possible to cancel the Lorenz forces by arranging plural pairs of electrodes and magnetic poles appropriately.

In this embodiment, the charged particle is then radiated to the magnetic poles 407 and 408 and electrode 409 and the magnetic poles 410 and 411 and electrode 412. Here again, the direction and the gradient of magnetic field line density generated by the magnetic poles 407 and 408 are opposite to those generated by the magnetic poles 410 and 411. Thus, by arranging plural pairs of a magnetic pole and an electrode appropriately, a force received from the magnetic field gradient can increase and a force, such as a Lorenz force, received from others can decrease, thereby allowing the magnetic moment resolution capability to be improved. From the standpoint of canceling the Lorenz force, the number of the combination of a magnetic pole and an electrode is preferably more than one. It goes without saying that the light axis 413 of the charged particles must be the same for every combination.

Embodiment 2

Figure 5:
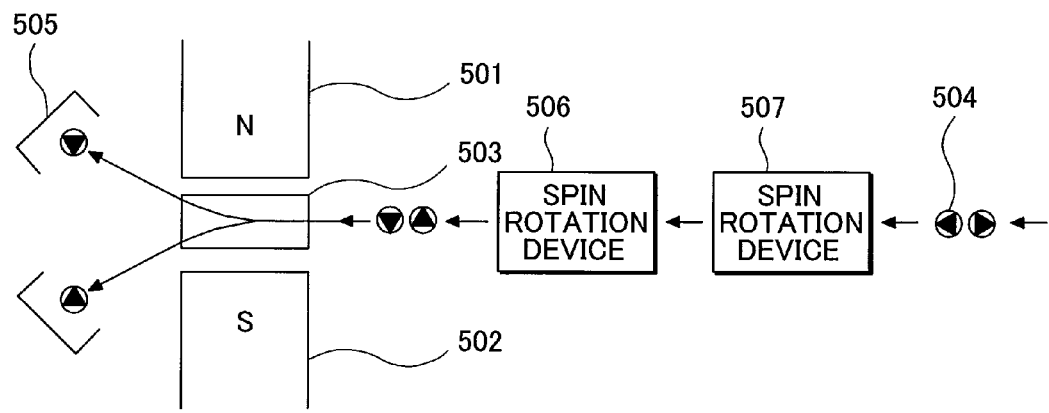
FIG. 5 shows the configuration of a charged particle spin polarimeter according to Embodiment 2.

FIG. 5 shows the configuration of Embodiment 2. With the technique described above, only the spin in a single direction perpendicular to the traveling direction of an electron beam can be resolved. To resolve a spin in another direction with a charged particle spin polarimeter, it is necessary to rotate the spin in an undetectable direction prior to radiation. This embodiment has a configuration wherein it is possible to detect a spin in another direction by disposing two spin rotation devices 506 and 507 before the charged particle spin polarimeter. As a spin rotation device, one having a similar structure to an energy analyzer called a Wien filter in which the electric field and the magnetic field bisect each other and the charged particle orbit at right angles (Rev. Sci. Instrum. 75, 2003 (2004)), a solenoid coil, and the like are conceivable.

With two Wien filters or the combination of a Wien filter and a solenoid coil, it is possible to direct an electron spin in any direction toward the direction in which the charged particle spin polarimeter of this embodiment can detect the spin. For example, in the case where the spin rotation device is not in operation, a spin component in the direction parallel to the magnetic field (vertical direction of the figure) can be detected in FIG. 5. Also, in the embodiment shown in FIG. 5, a spin component parallel to the charged particle orbit is detected. In addition, if the charged particle orbit is rotated vertically by 90 degrees about the rotation axis in FIG. 5, a spin component in the direction perpendicular to the drawing can be detected. By detecting these three directional spins, it is possible to determine the direction of the spin of a charged particle three-dimensionally.

Embodiment 3

Figure 6:
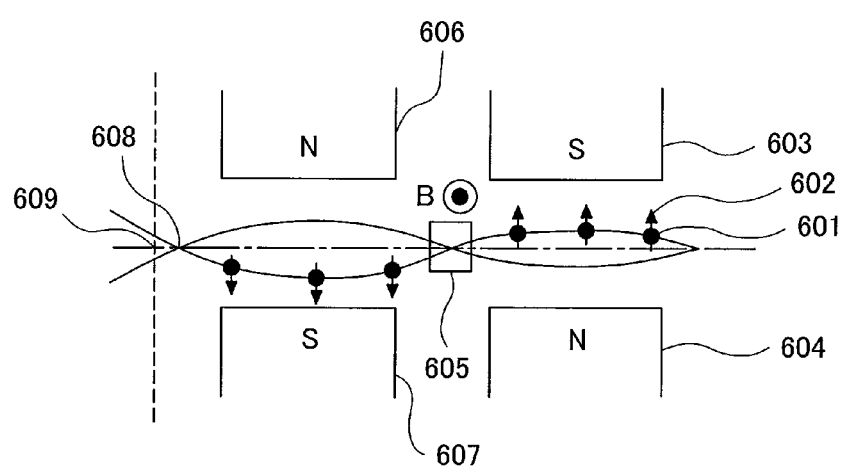
FIG. 6 shows the configuration of a charged particle spin polarimeter according to Embodiment 3.

FIG. 6 shows Embodiment 3 having a configuration in which the configuration of Embodiment 2 shown in FIG. 4 and the Lavi technique are combined. Here, a process in which a charged particle beam passes through a gradient magnetic field with convergent action being given is considered. The charged particle 601 moves from right to left direction in this figure, has the magnetic moment 602, and passes between the magnetic poles 603 and 604 generating a magnetic gradient, as in the embodiment described above. The electrode to cancel the Lorenz force is not shown in this figure. For example, it is assumed that the charged particle 601 has received a force in the upward direction in this figure due to the interaction between the magnetic moment 602 and magnetic gradient. The charged particle 601 then passes through a region 605 to which a magnetic field is applied in the direction perpendicular to the drawing. Due to the magnetic field applied at this time, the magnetic moment rotates to precess. And then, at the stage where the magnetic moment is reversed by adjusting the strength of the magnetic field, the charged particle is passed again between the magnetic poles 606 and 607 generating the magnetic field gradient. This magnetic field gradient within the magnetic poles 606 and 607 are, by reversing the polarity or reversing the direction of the gradient opposite to those of the magnetic poles 606 and 607, designed so that the reversed magnetic moment 602 receives an upward force from the magnetic field gradient as in the prior stage.

By passing the charged particle through the two-staged magnetic field gradient like this, the orbit of the charged particle 601 slightly shifts upwardly. Unless the charged particle 601 has magnetic moment, the charged particle beam is focused to the convergent point 609, but, depending the magnitude of the magnetic moment, reaches the position 608 away from the convergent point 609. Thus, by examining the convergence characteristic of a charged particle bean at the convergent point, it is possible to draw out the information on the magnitude and direction of a magnetic moment. Although two pairs of magnetic poles are used in this embodiment, more than two pairs may be used, and increasing the number of pairs has an advantage that the shift of the charged particle convergent point from magnetic moment can be increased.

Embodiment 4

Figure 7:
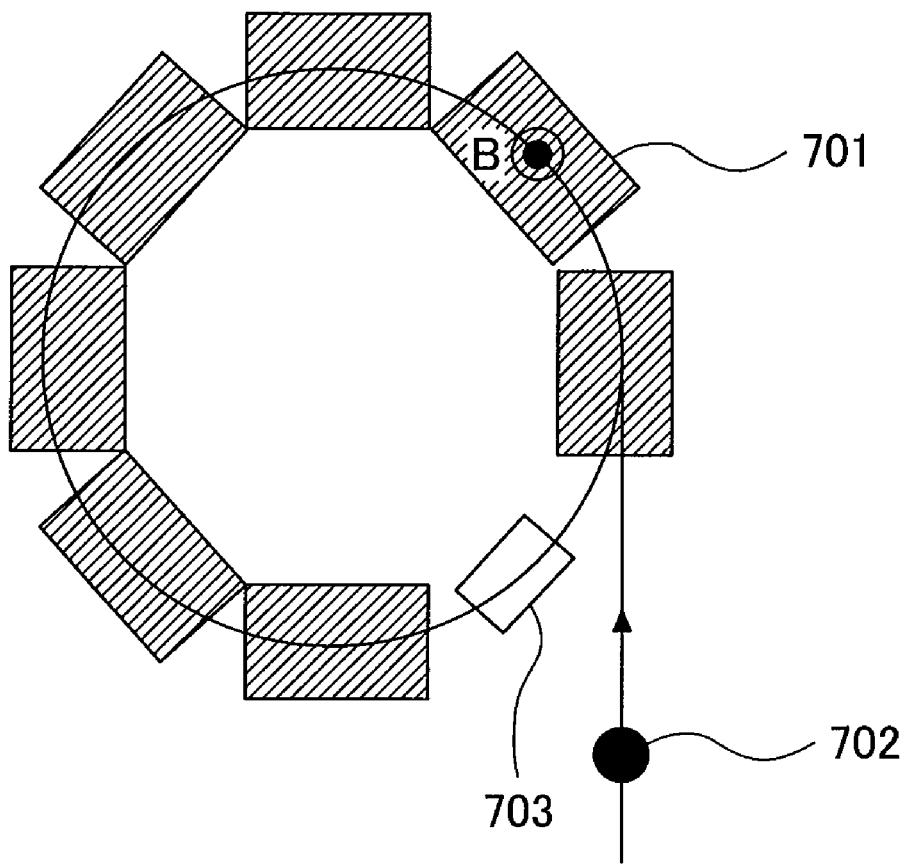
FIG. 7 shows the configuration of a charged particle spin polarimeter according to Embodiment 4.

FIG. 7 shows the configuration of Embodiment 4. The magnetic poles generating magnetic gradient and the electrode to cancel the Lorenz force a charged particle receives form one unit and plural units are arranged in a circle. However, it is necessary to leave a space for the incident charged particle 702. It is possible to insert a magnetic pole to reverse the magnetic moment as shown in FIG. 6 in this unit. The charged particle 702 is radiated to this circle in this state to rotate the charged particle in the circle by controlling the magnetic field within the unit. In this embodiment, it is assumed that the magnetic field within the unit is directed in the direction perpendicular to the drawing and the magnetic moment in this direction is resolved. Although a force the magnetic moment within each unit is weak, since the charged particle circulate several times and passes through the plural units arrange in the circle, if a force the magnetic moment receives from magnetic gradient is appropriately integrated, it results in the large difference in orbit. If that change in orbit becomes substantially large, the charged particle is radiated to the charged particle polarimeter 703 located at a position that is slightly away from the charged particle orbit toward the direction perpendicular to the drawing and counted. Using this circular motion of a charged particle makes it possible to integrate a weak force and resolve magnetic moment.

Although an example of using seven units 701 is shown in FIG. 7, it goes without saying that the number of the unit is not limited to 7.

Embodiment 5

Figure 8:
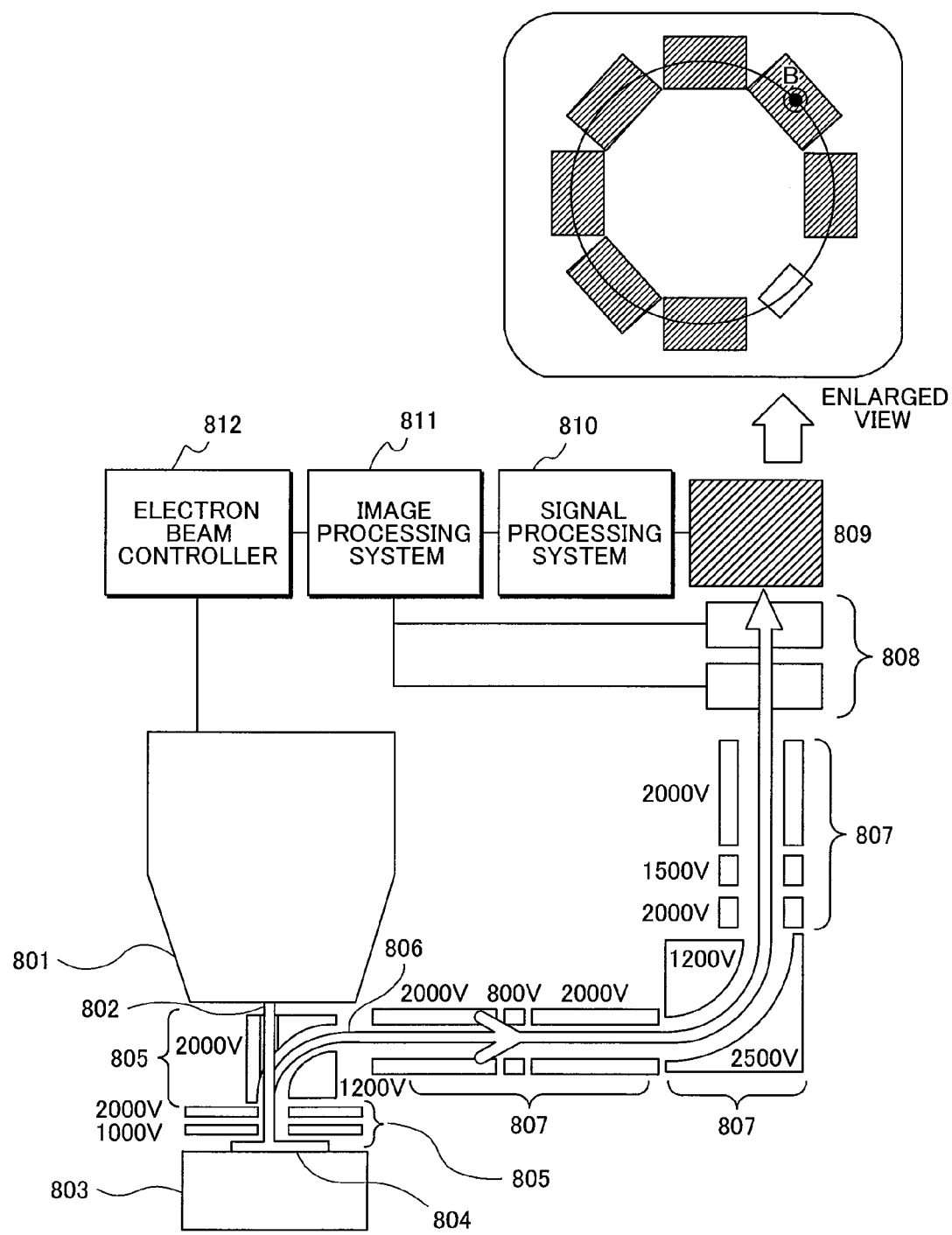
FIG. 8 shows the configuration of a spin-polarized scanning electron microscope equipped with a charged particle spin polarimeter according to Embodiment 5.

FIG. 8 shows an embodiment of a spin-polarized scanning electron microscope equipped with the charged particle spin polarimeter described above. The spin-polarized scanning electron microscope is an apparatus to obtain a magnetic domain by mapping the degree of spin polarization of a secondary electron emitted from a ferromagnetic sample, and the outline thereof is disclosed in JP-A 1985-177539 and others. A primary electron beam 802 emitted from the electron gun 801 is radiated to the sample 804 set on the sample stage 803. This is the same with an ordinary SEM so far, but with the spin-polarized scanning electron microscope it is necessary to dispose the secondary electron condensing optical system 805 in the vicinity of the sample to feed the secondary electron 806 as much as possible and resolve their spins. To this end, it is necessary to dispose the secondary electron feeding optical system 807 to feed the secondary electron 806 for feeding the secondary electron to the spin polarization system while adjusting the lens characteristic of these optical systems. An example of a voltage to be applied to the secondary electron condensing optical system 805 and the secondary electron feeding optical system 807 is shown in this figure.

The secondary electron 806 then reaches the spin rotation device 808 and is rotated by the charged particle spin polarimeter 809 to a direction in which components of the electron spin to be detected, and then fed to the charged particle spin polarimeter 809. If two spin rotation devices 808 are provided, it is possible to direct spins in any direction toward the detectable direction. It is desirable that the charged particle spin polarimeter 809 has such a configuration as shown in the enlarged view in this figure, also shown in FIG. 7 for Embodiment 4.

A signal from the charged particle spin polarimeter 809 enters the signal processing system 810 for signal processing, and a magnetic domain image is generated by the image processing system 811 for image processing. This image processing system 811 controls the spin rotation device 808 as well so that it is possible to select which directional spin to be imaged. Also, this image processing system 811 is connected to the electron beam controller 812 that controls the electron gun 801, and produces a magnetic domain image by integrating the position of the primary electron beam 802 on the sample and a signal from the signal processing system 810. A vacuum chamber enclosing the primary electron beam 802, sample stage 803, sample 804, secondary electron 806, secondary electron condensing optical system 805, secondary feeding optical system 807, spin rotation device 808, and charged particle spin polarimeter 809 is shown in this figure. Although the spin-polarized scanning electron microscope is an already known technology, it is possible to obtain data with substantially better S/N than conventional one, and also to provide a spin-polarized scanning electron microscope capable of obtaining a large amount of data in a short period.

Embodiment 6

Figure 9:
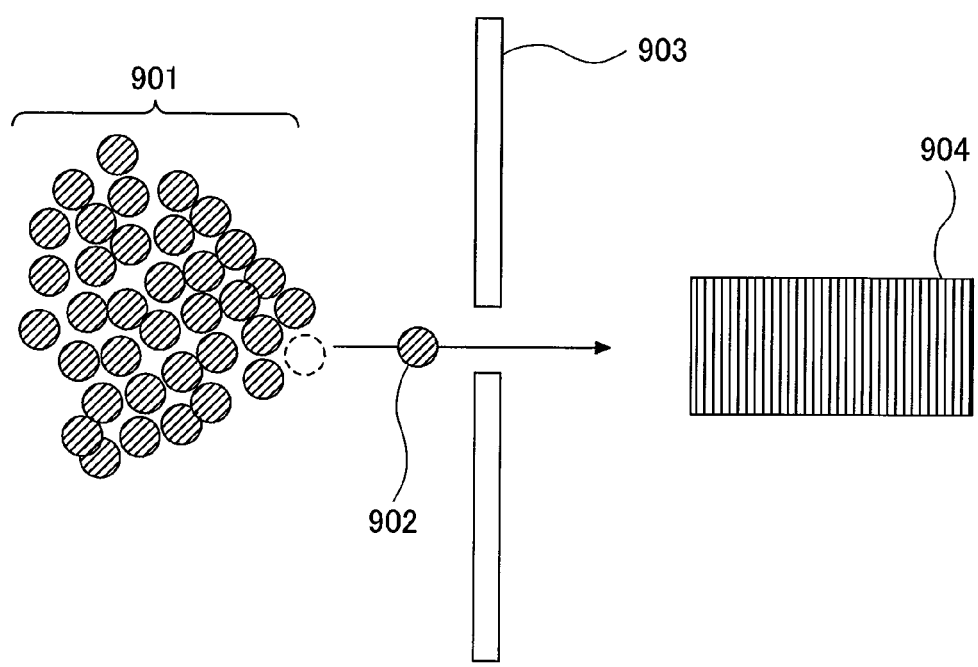
FIG. 9 shows the substantial part of an atom probe microscope or a field ion microscope equipped with a charged particle spin polarimeter according to Embodiment 6.

FIG. 9 shows an embodiment of an atom probe microscope or a field ion microscope equipped with a charged particle spin polarimeter. The atom probe microscope is for estimating the position and type of an atom by applying an electric field to a pointed sample and thereby measuring the emission direction and flight time of an atom to be emitted from the tip of the sample. The field iron microscope is basically the same as the atom probe microscope except that it does not measure the flight time. Such a sample 901 for the atom probe microscope is prepared and an electric field is applied thereto to cause the sample to emit the atom 902. Of the emitted atoms, an atom that flied out in a particular direction is selected using the aperture 903, and that atom is taken in the charged particle spin polarimeter 904. This allows the information on the magnetic moment of the atom to obtain through the measurement with the atom probe microscope or field ion microscope, and thereby the conventionally unavailable magnetization information on each atom can be obtained.

Embodiment 7

Figure 10:
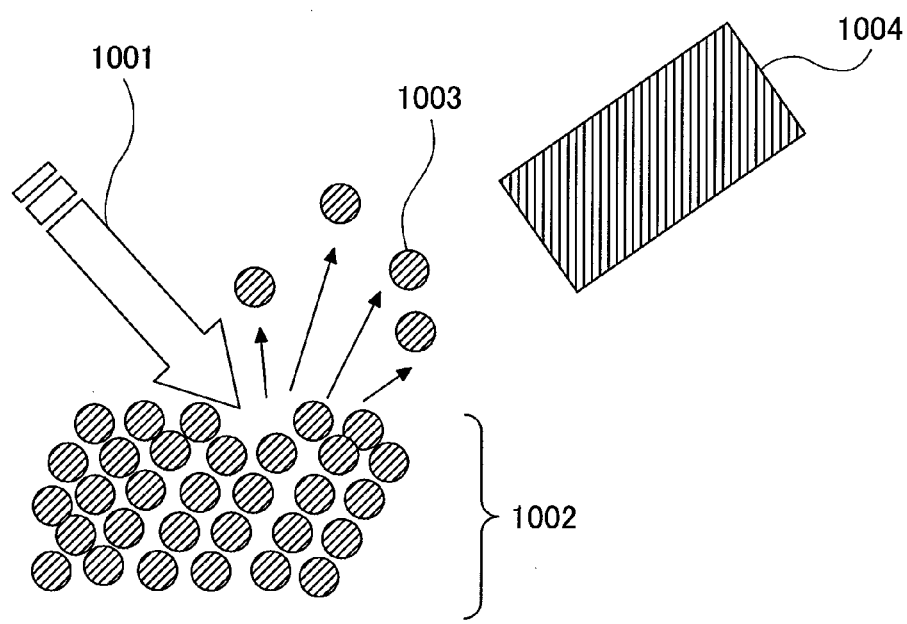
FIG. 10 shows the substantial part of a scanning ion microscopy equipped with a charged particle spin polarimeter according to Embodiment 7.

FIG. 10 shows an embodiment of a scanning ion microscope equipped with a charged particle spin polarimeter. When the accelerated ion beam 1001 is radiated to the sample 1002, the atoms in the surface of the sample are flicked out into a vacuum. If these atoms 1003 are taken in the charged particle spin polarimeter 1004 of the present invention, it is possible to obtain the information on the magnetization vector of the sample. Also, if incident ion beams are scanned in this method, the magnetic domain image on the surface of the sample can be obtained. At this time, electrons are also emitted from the inside of the sample by the ion beam 1001, and if these electrons are led to the charged particle spin polarimeter 1004 the similar information to that available from the spin-polarized scanning electron microscope can be obtained. It goes without saying that if the ion beam is replace with a primary electron beam in this embodiment, it becomes an embodiment of the spin-polarized scanning electron microscope.

Embodiment 8

Figure 11:
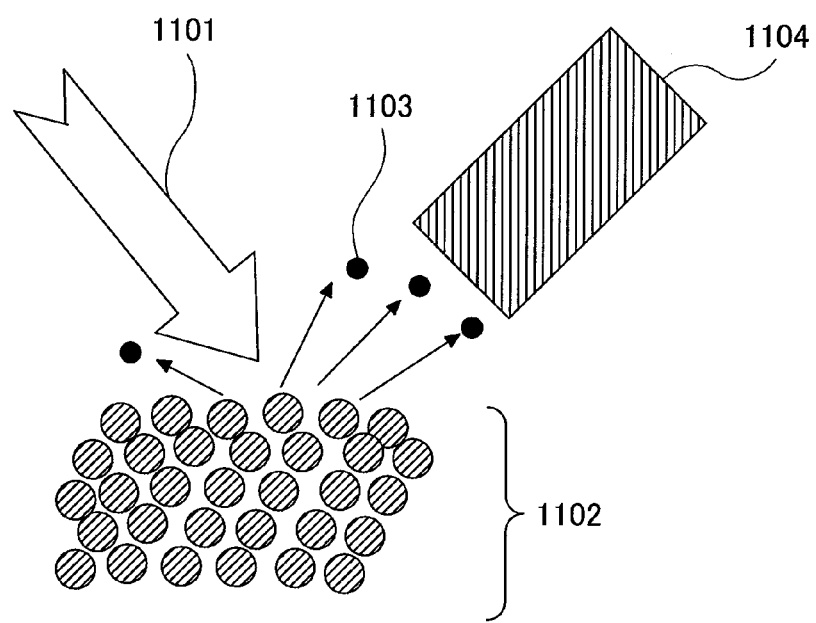
FIG. 11 shows the substantial part of a spin resolved photoelectron spectral device equipped with a charged particle spin polarimeter according to Embodiment 8.

FIG. 11 shows an embodiment of a photoelectron spectroscope equipped with a charged particle spin polarimeter. When the electromagnetic wave 1101 with a predetermined energy is radiated to the sample 1102, an electron at a level corresponding to the energy of the incident electromagnetic wave flies out into a vacuum as the photoelectron 1103. If this photoelectron 1103 is taken into the charged particle spin polarimeter 1104 of the present invention, the information on the magnetic moment of each element constituting the sample 1102 can be obtained. Although this method is known as spin resolved photoelectron spectrum (Jpn. J. Appl. Phys. 35, 6314 (1996)), conventionally the Mott polarimeter with insufficient sensitivity is used. By providing the charged particle spin polarimeter 1104 described above, it is possible to obtain data with substantially better S/N and also to obtain a large amount of data in a short period.

Embodiment 9

Figure 12:
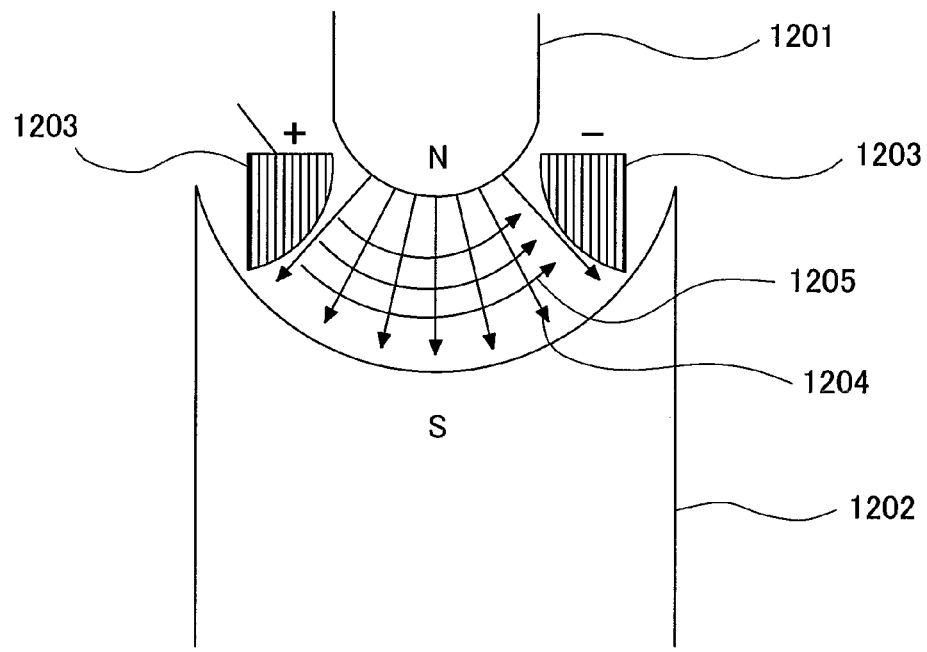
FIG. 12 shows the configuration of a charged particle spin polarimeter according to Embodiment 9.

FIG. 12 shows an embodiment for the preferred configuration of a charged particle detector. Although the magnetic pole 1201 of the N-pole and the magnetic pole 1202 of the S-pole are the same as the configuration shown in FIGS. 2A and 2B, the electrode 1203 generating an electric field to cancel a Lorenz force is hyperbolic column in shape, thus resulting in both magnetic field line 1204 and electric flux line 1025 being curved. This is because, in the field where an electric field and a magnetic field bisect each other and the orbit of a charged particle, the equi-electric potential plane or equi-magnetic potential plane are advantageous for the convergent action of charged particle beams (Rev. Sci. Instrum. 66, 5537 (1995)), and a similar effect can be expected with the charged particle spin polarimeter of the present invention.

Embodiment 10

Figure 13:
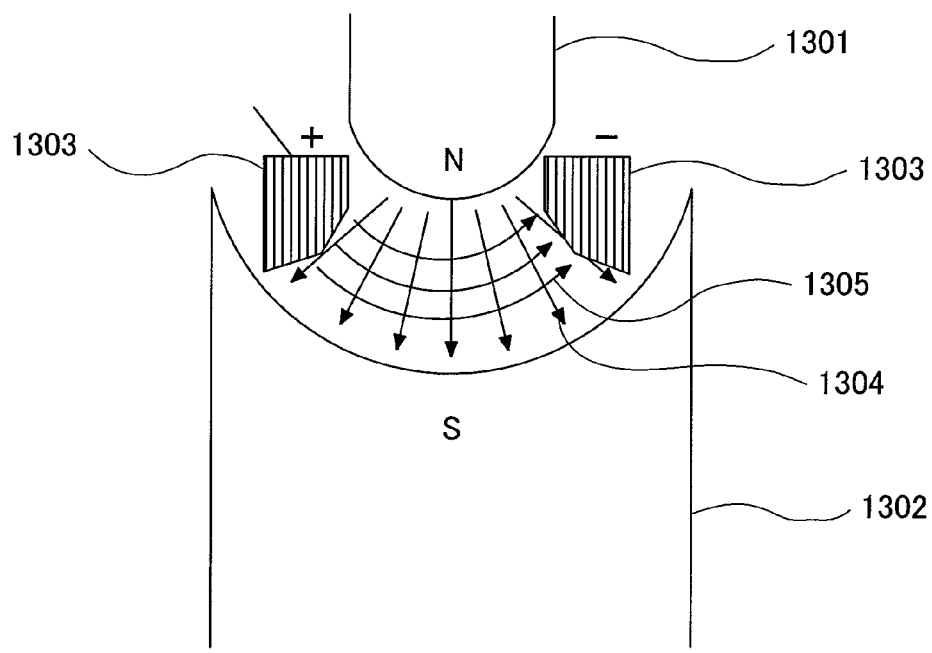
FIG. 13 shows the configuration of a charged particle spin polarimeter according to Embodiment 10.

FIG. 13 shows an embodiment for another configuration of a charged particle detector. Although the magnetic pole 1301 of the N-pole and the magnetic pole 1302 of the S-pole are the same as with the configuration shown in FIGS. 2A and 2B, the electrode 1303 generating an electric field to cancel a Lorenz force is column approximate to hyperbolic column in shape. It is not easy to precisely form the hyperbolic column shape shown in FIG. 12, but it is easy to approximate it with the column shape like this. As a result, both of the magnetic field line 1304 and the electric flux line 1305 become curved and thereby a similar effect can be obtained.

What is claimed is:
1. A charged particle spin polarimeter comprising
 a pair of magnetic poles to apply a magnetic field with gradient to an incident charged particle; and
 a pair of electrodes to apply an electric field to the charged particle for canceling a Lorentz force that the charged particle receives from the magnetic field, wherein one magnetic pole of the pair of magnetic poles has a concave surface on a side of the orbit of the charged particle, wherein the other magnetic pole of the pair of magnetic poles has a convex surface on another side of the orbit of the charged particle, wherein the pair of electrodes are arranged in a space defined by ends of the one magnetic pole having the concave surface, and wherein a magnetic moment in a magnetic field direction of the charged particle is resolved due to the interaction between the gradient of the magnetic field and a magnetic moment of the charged particle.

2. The charged particle spin polarimeter of claim 1, wherein the pair of electrodes are two plain plate electrodes disposed by inclining them against each other.

3. The charged particle spin polarimeter of claim 1, wherein the cross-section of the pair of electrodes is a hyperbolic or a square column shape.

4. The charged particle spin polarimeter of claim 1, wherein a plurality of the pairs of magnetic poles and a plurality of the pairs of electrodes are arranged in the traveling direction of the charged particle, and the polarity of the arranged plurality of the pairs of magnetic poles and the polarity of an electric potential to be applied to the pairs of electrodes are different with respect to the traveling direction of the charge particle.

5. A charged particle spin polarimeter, comprising:
a pair of magnetic poles to apply a magnetic filed with gradient to an incident charged particle; and
a pair of electrodes to apply an electric field to the charged particle for canceling a Lorentz force that the charged particle receives from the magnetic field,
wherein a magnetic moment in a magnetic field direction of the charged particle is resolved due to the interaction between the gradient of a magnetic field and magnetic moment of the charged particle,
wherein a plurality of the pairs of magnetic poles and a plurality of the pairs of electrodes are arranged in the traveling direction of the charged particle, and the polarity of the arranged plurality of the pairs of magnetic poles and the polarity of an electric potential to be applied to the pairs of electrodes are different with respect to the traveling direction of the charge particle, and
wherein a plurality of the pairs of electrodes and a plurality of the pairs of magnetic poles are arranged in a circle, and magnetic moment resolution effect due to the gradient of a magnetic field is increased by rotating the orbit of a charged particle several times in the circle.

6. The charged particle spin polarimeter of claim 1, wherein a mechanism is provided that rotates the direction of charged particle spin before the charged particle is radiated to the charged particle spin polarimeter, and thereby it is possible to detect charged particle spin in any direction using the mechanism.

7. The charged particle spin polarimeter of claim 6, wherein the mechanism for rotating the direction of charged particle spin includes that of Wien filter type in which an electric field and a magnetic field bisect each other.

8. The charged particle spin polarimeter of claim 6, wherein the mechanism for rotating the direction of charged particle spin is composed of two spin rotation devices, and at least one of the spin rotation devices is of a Wien filter type.

9. A spin resolved photoelectron spectroscope equipped with the charged particle spin polarimeter described in claim 1.

10. An atom probe microscope equipped with the charged particle spin polarimeter described in claim 1.

11. A field ion microscope equipped with the charged particle spin polarimeter described in claim 1.

12. A scanning ion microscope equipped with the charged particle spin polarimeter described in claim 1.

13. A spin-polarized scanning electron microscope equipped with the charged particle spin polarimeter described in claim 1.

14. A spin-polarized scanning electron microscope comprising:
an electron gun to emit a primary electron beam;
a sample stage where a sample to which the primary electron beam is radiated is placed;
a secondary electron condensing optical system that converges secondary electrons emitted from the sample by radiating the primary electron beam;
a secondary electron feeding optical system that feeds the condensed secondary electrons;
a spin polarimeter to detect spin polarization of the fed secondary electrons; and
a signal processing section that processes an output signal from the spin polarimeter,
the spin polarimeter being equipped with a pair of magnetic poles to apply a magnetic field with gradient to the secondary electron; and a pair of electrodes to apply to the secondary electron an electric field that cancels a Lorentz force that the secondary electron receives from the magnetic field,
wherein one magnetic pole of the pair of magnetic poles has a concave surface on a side of the orbit of the charged particle,
wherein the other magnetic pole of the pair of magnetic poles has a convex surface on another side of the orbit of the charged particle, and
wherein the pair of electrodes are arranged in a space defined by ends of the one magnetic pole having the concave surface.

15. The spin-polarized scanning electron microscope of claim 14, wherein a mechanism for rotating the direction of electron spin of the secondary electron is disposed between the secondary electron feeding optical system and the spin polarimeter.

* * * * *